United States Patent [19]

Gupta

[11] Patent Number: 4,834,750
[45] Date of Patent: May 30, 1989

[54] DEFORMABLE-ELASTIC INTRAOCULAR LENS

[75] Inventor: Amitava Gupta, Pasadena, Calif.

[73] Assignee: Ioptex Research, Inc., Azusa, Calif.

[21] Appl. No.: 99,293

[22] Filed: Sep. 17, 1987

[51] Int. Cl.$^4$ .......................... A61F 2/16; B29D 11/00
[52] U.S. Cl. ........................................... 623/6; 264/1.7
[58] Field of Search ....................... 623/6; 264/1.1, 1.7

[56] References Cited

U.S. PATENT DOCUMENTS 4,668,446  5/1987  Kaplan et al. ..................... 623/6 X
4,731,079  3/1988  Stoy ........................................ 623/6

Primary Examiner—Ronald L. Frinks
Attorney, Agent, or Firm—Robert R. Meads

[57] ABSTRACT

A deformable-elastic intraocular lens comprising a deformable-elastic lens body of crosslinked acrylic material formed of copolymers of methacrylate and acrylate esters which are relatively hard and relatively soft at body temperature, crosslinked with a diacrylate ester to produce an acrylic copolymer having a substantially tack-free surface, a crosslink density of between $0.5 \times 10^{-2}$ and $1.5 \times 10^{-2}$ moles per liter, and glass transition temperature in the range of $-30°$ C. to $25°$ C., a tensile modulus between 1000 and 3000 psi and a elongation a break of 100% or greater.

21 Claims, 3 Drawing Sheets

DEFORMABLE-ELASTIC INTRAOCULAR LENS

BACKGROUND OF THE INVENTION

The present invention relates generally to improvements in intraocular lenses (IOLs) designed for surgical implantation into the eye, for example, as a replacement for a cataractous or injured natural lens. More specifically, the invention relates to improvements in deformable IOLs which can be folded or rolled to a relatively low profile size to fit into the eye through a relatively small incision, and then within the eye naturally return to an initial nondeformed shape with predetermined optical properties.

IOLs are well known in the art for implantation into the eye as a replacement for a natural crystalline lens which has been surgically removed typically due to opacification, commonly referred to as a cataract condition. Such IOLs have been formed from a small disk of transparent glass or plastic material having appropriately shaped lens surfaces to achieve a desired set of optical properties. The IOL is implanted directly into the eye, typically after removal of the natural crystalline lens, via an incision formed in ocular tissue such as the sclera outside the normal line of sight. Many IOLs are designed for implantation into the so-called posterior chamber of the eye behind the iris and pupil, whereas other IOLs are adapted for placement into the anterior chamber in front of the iris and pupil. In most IOL designs, support structures are attached to or formed integrally with a central lens body or optic and project outwardly therefrom to contact eye tissue at the periphery of the posterior or anterior chamber, thereby retaining the lens body or optic in generally centered relation with the line of sight passing through the pupil.

In the past, most IOLs have been formed from polymethylmethacrylate (PMMA) which is relatively light in weight, possesses excellent optical properties, and is generally considered to be relatively inert when implanted into the eye, thereby avoiding adverse tissue reactions. However, PMMA comprises a plastic matrix which, when formed into the shape of a lens, possesses high rigidity and cannot be deformed by folding, rolling, compression, etc. Accordingly, the use of PMMA lenses requires a relatively large incision in the ocular tissue sufficient to accommodate the entire diametric size of the lens body; which is typically six millimeters or larger, together with the accompanying lens support structures. Although resilient lens support structures such a polypropylene loops or haptics are commonly used and advantageously may be folded over the lens body during insertion, such resilient haptics are anchored into the periphery of the hard plastic lens body and thus tend to spring back to their initial unfolded shape with a rapid snap like action during IOL implantation, resulting in undesired trauma to sensitive eye tissues.

While IOLs with rigid PMMA lens bodies have gained widespread acceptance and use, it has been recognized that deformable IOLs have the potential of providing medical benefits well beyond those associated with current IOLs including rigid lens bodies. More particularly, an IOL including a deformable transparent lens body which may be folded or rolled into a reduced profile size may fit through a relatively small incision in ocular tissue and after insertion and release within the eye return to its original size and shape by virtue of its natural resilience. The use of a smaller incision would beneficially result in a safer overall surgical procedure requiring fewer stitches and reduced likelihood of postoperative complications such as infections. In addition, a smaller incision would reduce the incidence of postoperative astigmatism and substantially reduce rehabilitation time. Second, it is anticipated that IOLs with deformable lens bodies may reduce the potential for complications secondary to contact or rubbing against delicate uveal tissues. Also, deformable IOLs may decrease the potential for pigmentary dispersion or pigmentary glaucoma. Finally, it is anticipated that the formable IOLs will provide an added margin of safety for patients with blood dyscrasias, coagulopalthies and hematologic matogrant disease as well as those patients being given anti-coagulant therapy.

Accordingly, deformable IOLs formed of silicones and hydrogels have been proposed for implantation. For example, in 1983, Fyodorov reported on chemical testing of a silicone IOL (Fyodorov, S. W. et al "Initial Clinical Testing of a Silicone Intraocular Lens" Interzonal Scientific/Practical Conference of Ophthalmologists of Western and Eastern Siberia and the Far East, Conference Proceedings 4: 22–24, 1983, Vladivostock). Also in 1983, Mazzacco and Davidson presented initial data on the implantation of silicone IOLs with 6 mm optical zones through 3 mm incisions (Mazzacco, T. R. and Davidson, V. A. "6 mm Optic for a 3 mm Wound" presented at the A.I.O.I.S. United States Intraocular Lens Symposium, New Orleans, La., March 1983). Wichterle and his associates developed a hydrogel of hydrophilic polyacrylates for orbital and intracameral implants in 1960 while Epstein implanted flexible IOLs comprised of poly(hydro hydroxyethyl methacrylate) in 1976 and 1977. The condition of some patients implanted with such lens was followed until 1984 ("Insertion Techniques and Clinical Experience with HEMA Lenses" *Soft Implant Lenses in Cataract Surgery* T. R. Mazzacco, G. M. Rajacich, E. Epstein, published by Slack Inc., 1986, pp. 11).

Unfortunately, silicones and hydrogels have several well documented deficiencies which hinder their use as IOL materials. In particular, silicones cause complement activation leading to the production of C-4 proteins, a symptom of bio-incompatibility. Also, while silicones may be folded, when released they tend to snap back or regain their unfolded shape too rapidly, posing a threat to the integrity of the endothelial cell layer of the eye. In addition, the long term stability of UV-absorbing silicone formulations is uncertain. As for hydrogels, it has been found that hydrogel materials when hydrated vary in composition including water content from lot to lot. Such variability induces a corresponding variability in the refractive power of IOL lens bodies formed of hydrogel material. Therefore, hydrogel IOLs need to be hydrated in order to determine their refractive power in an implanted state. Unfortunately, hydrated lenses cannot be safely stored in the wet state without losing sterilization. If they are dehydrated subsequently, the process of hydrothermal cycling reduces the tensile strength of the IOL material and may cause cracks or crazes to develop in the lens body.

Other deformable IOLs have been described in U.S. Pat. Nos. 4,573,998 and 4,608,049. More specifically, the '998 patent is directed to methods for implantation of deformable IOLs. The patent describes an IOL having an optical zone portion composed of materials such as polyurethane elastomers, silicone elastomers, hydrogel polymer collagen compounds, organic or synthetic gel compounds and combinations thereof. In practice, such materials possess the disadvantages previously attributed to silicone and hydrogel materials.

The '049 patent describes two basic types of deformable IOLs. The first type includes a lens body of one or more rigid portions hinged or otherwise connected to overlap each other when it is desired to reduce the profile of the lens body as during implantation of the lens. Such lens configurations are difficult to construct and to manipulate during implantation and further suffer from the limitations associated with rigid IOLs. The second type of IOL described by the '049 patent includes a deformable lens body characterized as being capable of return to an undeformed configuration after insertion into the eye. The lens body may be of silicone rubber or an acrylate polymer with ethylene glycol dimethacrylate as a crosslinking agent producing a material of a rubber consistency. The deformable lens body is secured to an L-shaped fixation member around which it may be curled during insertion into the eye. The silicone rubber IOL of the '049 patent suffers from the limitations previously attributed to silicone IOLs. The acrylate polymer lens body described in the '049 patent is a hydrogel of a relatively hard consistency (subject to the foregoing problems attributed to hydrogels) while other acrylate polymers known to be pliable are prone to mechanical failure upon compression or folding and are subject to degradation in the eye.

In view of the foregoing, it is apparent that there is a need for an intraocular lens and lens material having an improved balance of superior optical characteristics, flexibility, elasticity, elastic memory, and tensile strength. The present invention satisfies such needs.

SUMMARY OF THE INVENTION

Generally speaking, the present invention comprises an IOL having a deformable-elastic transparent lens body of crosslinked acrylic material having a tensile strength sufficient to resist deformation after implantation into the eye as by forces exerted by growing tissue around the IOL; a flexibility as measured by elongation at break sufficient to allow the lens body to be readily folded, rolled or otherwise deformed to a low profile condition for implantation through a small incision into the eye; an elastic memory which enables the folded lens body to naturally and at a controlled rate return to its original shape and optical resolution without damaging or otherwise traumatizing eye tissue; and a low-tack surface which will not stick to surgical instruments used to hold and guide the lens body during insertion and positioning within the eye. In particular, the crosslinked acrylic material comprises copolymers of methacrylate and acrylate esters which are relatively hard and relatively soft at body temperature, crosslinked with a diacrylate ester to produce an acrylic material having a substantially tack-free surface, a crosslink density between $0.5 \times 10^{-2}$ and $1.5 \times 10^{-2}$ moles per liter, a glass transition temperature in the range of $-30°$ to $25°$ C., a tensile modulus in the range of 1000 to 3000 psi and an elongation at break of between 100 and 300%. Such a lens body is easily folded, rolled or otherwise deformed into a low profile for insertion through a small incision and after insertion will naturally return to its original optical resolution at a slow controlled rate in between 20 and 180 seconds even if the lens body has been deformed to a low profile condition for an extended period of time. The slow return allows the surgeon adequate time to locate the folded IOL in the eye before the lens body returns to its original shape and resolution and insures that the unfolding of the lens will not damage or otherwise traumatize ocular tissue. Furthermore, a lens body of the foregoing material and composition possesses a desired tensile strength to resist deformation in response to forces exerted by tissue growing around the implanted lens body thereby maintaining the desired optical characteristics and resolution of the lens body.

Preferably, in the formation of the deformable-elastic acrylic material, the copolymers of methacrylate and acrylate esters are mixed at approximately a 45 to 55 weight percent ratio and the relatively hard methacrylate ester is a fluoroacrylate. The fluoroacrylate functions as a surface energy lowering agent as well as a monomer providing long term stable inertness and tensile strength to the polymer without adversely effecting the pliancy of the resulting material. In this regard, the fluoroacrylate is present in a concentration range by weight of between 5 and 25% and preferably is trifluoro ethyl methacrylate. Also in the preferred formulation of the crosslinked acrylic, the mixture of the copolymers is partially polymerized prior to chemical crosslinking with diacrylate ester in a concentration range of between 0.5 and 3.0 percent by weight.

The resulting crosslinked acrylic material may be molded and formed into lens bodies machined to have the desired optical characteristics and resolution with haptics extending therefrom either integral with or separately attached to the lens body. Preferably, the crosslinked acrylic material formed according to the present invention is machined and otherwise processed at low temperatures in the range of $-80°$ to $-10°$ C. and preferably at $-60°$ C. In particular, during cutting the lens body is maintained at a temperature below its Beta-relaxation temperature where the material is even harder than at its glass transition temperature.

BRIEF DESCRIPTION OF THE DRAWINGS

The accompanying drawings illustrate the invention. In such drawings:

FIG. 9 also illustrates a plan view of the part produced from such a mold.

DETAILED DESCRIPTION

As shown in the exemplary drawings, one preferred form of an improved IOL is referred to generally by the reference number 10 in FIGS. 1-5. The improved lens 10 is deformable (FIGS. 4 and 5) to a reduced profile size to permit implantation into an eye 12 through a relatively small incision 14. The lens 10 is formed with a selected set of physical characteristics to expand within the eye slowly but substantially completely to its initial nondeformed state and optical resolution without trauma to delicate eye tissue.

Figure 1:
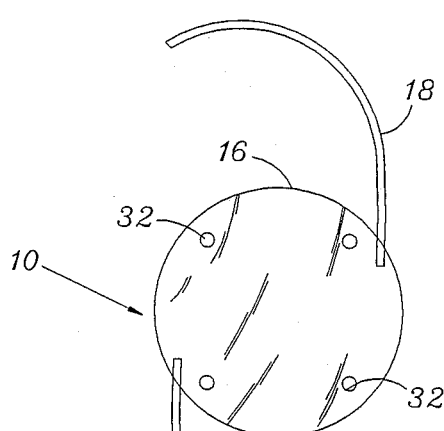
FIG. 1 is a front elevation view of an exemplary IOL formed in accordance with the novel features of the invention.
Figure 3:
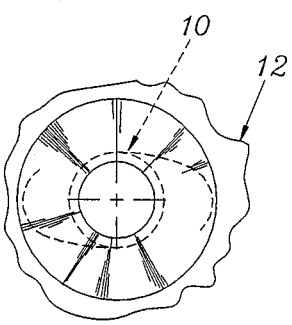
FIG. 3 is a fragmented front elevation view depicting the IOL of FIG. 1 implanted into the posterior chamber of an eye.
Figure 2:
FIG. 2 is a side elevation view of the IOL depicted in FIG. 1.

As shown in FIGS. 1, 2 and 3, the IOL 10 of the present invention comprises a traditional disk-shaped lens body 16 having an appropriate diametric size typically on the order of about six millimeters and a combination of surface shapes on the anterior-posterior sides to provide selected dioptric characteristics, with a convexo-plano shape being shown by way of example in the illustrative drawings. The IOL 10 is adapted for implantation into the eye 12 subsequent to surgical removal of the natural crystalline lens, typically due to a cataract condition. Alternately, if desired, the IOL can be implanted to obtain refractive correction of the natural lens. Support structures such as a pair of outwardly radiating and curved resilient loops or haptics 18 are secured to the lens body 16 and function to support the lens body within the eye 12, as will be described in more detail. The haptics 18 may be anteriorly angulated as shown in FIG. 2, and/or provided in other configurations such as a trio of loops or alternate support structures formed integrally with the lens body, in accordance with the particular intraocular lens design.

Figure 5:
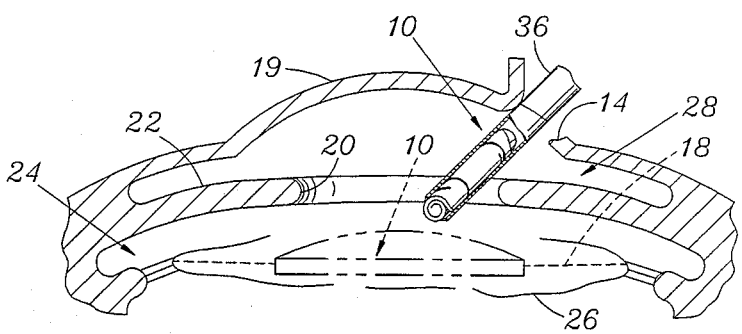
FIG. 5 is a fragmented sectional view illustrating implantation of the lens into the posterior chamber of the eye.

In accordance with known intraocular lens implantation techniques, the IOL 10 is adapted for implantation into the eye through an incision 14 formed in the ocular tissue at a position removed from a normal sight line passing through the transparent cornea 19, as viewed in FIG. 5, and further through the pupil 20 defined by the iris 22. The IOL 10 can be designed as shown in FIG. 5 for implantation through the pupil 20 into the so-called posterior chamber 24 behind the iris 22, typically within a capsular bag 26 which has been anteriorly ruptured in the course of extracapsular extrusion of the natural crystalline lens. Alternately, if desired, the IOL 10 can be implanted into the anterior chamber 28 at the front side of the iris 22. In either case, support structures such as the illustrative pair of outwardly curving support loops 18 seat against surrounding tissue at the chamber periphery to retain the lens body 16 generally centered on the normal line of sight. Positioning holes 32 may also be provided near the periphery of the lens body 16 and are easily engaged by appropriate surgical instruments (not shown) to facilitate lens manipulation by the surgeon to the desired position within the eye.

Figure 4:
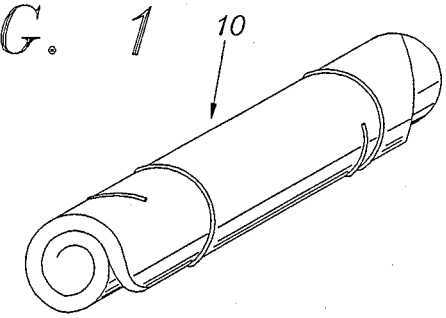
FIG. 4 is an enlarged perspective view illustrating the lens of FIG. 1 rolled into a reduced size profile prior to implantation.

In accordance with primary aspects of the invention, the lens body 16 of the IOL 10 is formed from a deformable-elastic transparent crosslinked acrylic material with a unique balance of flexibility, elasticity, tensile strength and softness properties yielding significant advantages during implantation and subsequent use. More specifically, because of its improved flexibility, the IOL is capable of being reduced in profile size to fit through the incision 14 of reduced size in comparison with conventional hard plastic lens of polymethylmethacrylate (PMMA) or the like. Because of its controlled elasticity, the lens body 16 anchors the haptics 18 with sufficient damping to prevent rapid or snap-action movement of the haptics 18 toward their normal unstressed configurations, thereby preventing the haptics from sharply striking and damaging eye tissue. Moreover, the lens body possess a relatively slow speed of return or retraction of about twenty (20) to one-hundred eighty (180) seconds from a deformed state as shown in FIG. 4 to its initial undeformed state to avoid striking and damaging eye tissue. Further, the lens body has excellent elastic memory to insure substantially complete return to the undeformed state without plastic deformation.in the form of fold lines or creases or other distortions which would otherwise impair optical quality.

Figure 6:
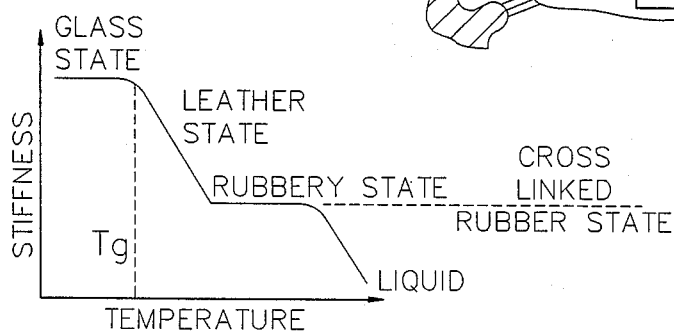
FIG. 6 is a graphic representation of the relative stiffness of the body of the IOL as a function of temperature.

The preferred crosslinked acrylic material for the IOL 10 comprises copolymers of methacrylate and acrylate esters which are relatively hard and relatively soft at body temperature, partially polymerized, chemically crosslinked with a diacrylate ester and cured. The resulting acrylic has a relatively leathery characteristics at temperature conditions corresponding with or approximating body temperature. More specifically, with reference to FIG. 6, the crosslinked acrylic composition is selected to have a glass transition temperature (Tg) somewhat below body temperature so that the lens will exhibit a stiffness (Young's modulus) at a body temperature environment reflecting a relatively leathery characteristic. In addition, the crosslinked acrylic composition is chosen to have highly elastic or viscoelastic properties with substantially no plastic deformation and a relatively slow speed of retraction. With such a combination of characteristics, the IOL 10 can be deformed as by rolling upon itself together with the haptics 18 as viewed in FIGS. 4 and 5 for facilitated implantation via a small insertion tube 36 passed through the small incision 14. In particular, the hollow insertion tube 36 may be prefilled with Healon or the like for lubrication purposes. The IOL 10, including the lens body 16 and haptics 18, may be temperature prepared in advance substantially at body temperature, at which time the IOL 10 and tube 36 are advanced through the incision 14 and into the eye, for example, within the posterior chamber 24, where the lens is expelled from the tube 36 within the eye. The thus-released lens is allowed to return to its initial nondeformed state. Importantly, this return movement takes place slowly with excellent elastic memory over a time of at least about twenty seconds. When the lens is substantially completely expanded, the lens position within the eye can be manipulated with appropriate instruments engaging, for example, the positioning holes 32 after which the incision is closed to complete the procedure.

The preferred lens body composition is prepared by copolymerization of transparent acrylic and methacrylic monomers which otherwise exhibit relatively hard and relatively soft physical characteristics in a body temperature environment and a glass transition temperature (Tg) within the range of about $-30°$ to about $25°$ C. and more preferably $0°$ C. Preferably, the monomers include a fluoromonomer for enhancing the tack-free inertness and tensile strength characteristics of the lens body within the eye and the resulting acrylic is produced by chemical crosslinking with a diacrylate ester to form a stable interpenetrating polymer network having the desired elasticity and elastic memory characteristics.

The following chart lists various monomers which after purification, as by vacuum distillation, may be used in preparing the desired copolymer of crosslinked acrylic material as well as the concentration ranges for such monomers in percent by weight and preferred compositions I and II in percent by weight composition.

| Monomer | Concentration Range % | Preferred Compositions % | |
|---|---|---|---|
| | | I | II |
| Ethyl Methacrylate | 25–45 | 34 | 34 |
| Trifluoro Ethyl Methacrylate | 5–25 | 10 | 10 |
| n-Butyl Acrylate | 30–60 | 52 | 0 |
| Ethyl Acrylate | 30–60 | 0 | 52 |
| 2-Ethyl Hexyl Acrylate | 30–60 | 0 | 0 |
| 2-Hydroxy 4-Ethyloxy-Acryloxy Benzophenone (UV-2098) | 0–10 | 1.5 | 1.5 |
| 2, 5 Dimethyl-2,5 Bio (2-Ethyl Hydroxyl Droxyl) Hexane (USP 245) | 0.05–0.2 | 0.15 | 0.15 |
| Ethylene Glycol Dimethacrylate | 0.5–3.0 | 2.5 | 2.5 |

Figure 7:
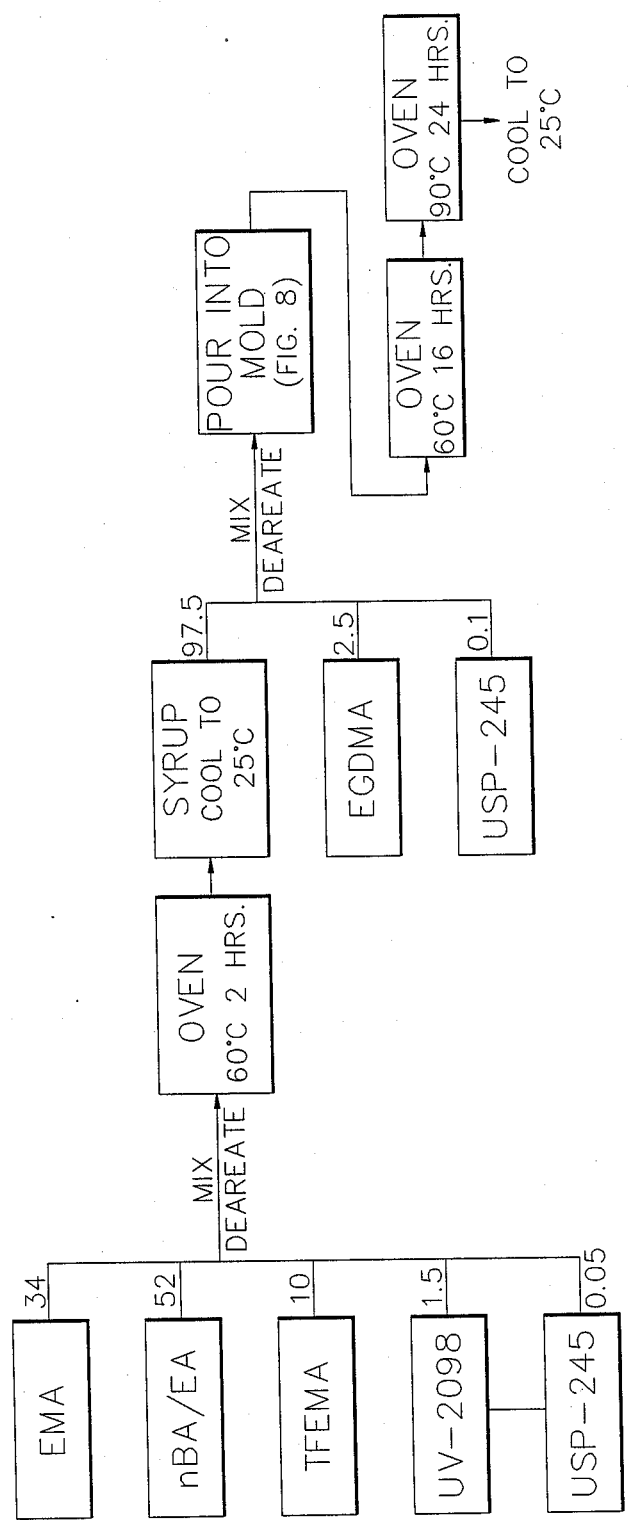
FIG. 7 is a flow diagram in block form illustrating a preferred form of a method for producing a deformable-elastic acrylic material comprising a lens body of an IOL in accordance with the present, invention.

A preferred form of the method for forming the copolymer is depicted in FIG. 7. As there represented, ethyl methacrylate is mixed with n-butyl acrylate or ethyl acrylate preferably in a weight percent concentration of 34% to 52% respectively. In addition to the methacrylate and acrylate esters of ethyl methacrylate and n-butyl acrylate or ethyl acrylate, the mixture includes 10% by weight of a fluoroacrylate functioning as a surface energy lowering agent. Such fluoroacrylates may be perfluoro octal methacrylate or more preferably trifluoroethyl methacrylate. In the mixture, the n-butyl acrylate or ethyl acrylate provides flexibility in the presence of methacrylate esters principally because of the low glass transition temperature thereof. However, the n-butyl acrylate or ethyl acrylate renders the mixture tacky or sticky. Such tackiness is minimized by the fluoroacrylate particularly trifluoroethyl methacrylate. In addition to the foregoing, and as represented in FIG. 7, the mixture includes a UV-absorber, UV-2098 and a free radical initiator, preferably USP 245, which is one in a class of aliphatic peroxides. The UV-absorber and initiator are present at 1.5 and 0.05% by weight concentrations. The combination is mixed, deareated and placed in an oven at about 60° C. for two hours. The mixture undergoes partial polymerization to form a viscous syrupy liquid when cooled to about 25° C. The viscous syrupy liquid may be stored for several days at −15° C. for subsequent mixing with a crosslinking agent and free radical initiator.

An alternate method of preparing the syrup is to dissolve low molecular weight (number average molecular weight between 30,000–50,000) polymers such as poly(ethyl methacrylate) and poly(n-butyl acrylate) in the same relative concentrations at a polymer - monomer ratio ranging from 1:5 to 1:3. The syrup may be filtered through a 0.2 micron filter immediately prior to use.

Again, as represented in FIG. 7, the crosslinking agent may consist of ethylene glycol dimethacrylate. Alternatively, the crosslinking agent may be propylene glycol dimethacrylate or ethylene glycol diacrylate. In each case, the crosslinking agent is mixed in a weight percent concentration of about 2.5 to produce a crosslinked density for the resulting copolymer in a range of $0.5 \times 10^{-2}$ to $1.5 \times 10^{-2}$ moles per liter. Such a crosslinking density provides the resulting polymer with the desired elastic memory and elasticity. In particular, upon being folded, the resulting lens bodies 16 will return to its initial state naturally in about 20 to 180 seconds and preferably about 30 seconds.

Figure 8A:
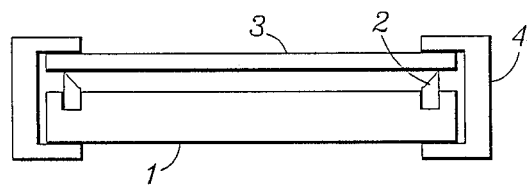
FIGS. 8A and 8B illustrate two molds useful in the method of the present invention for forming acrylic material into intraocular lens bodies.
Figure 8B:
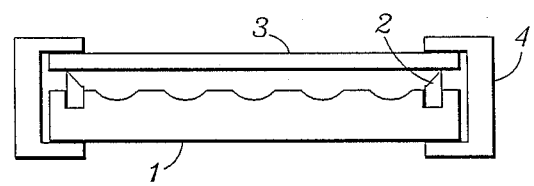
Figure 9:
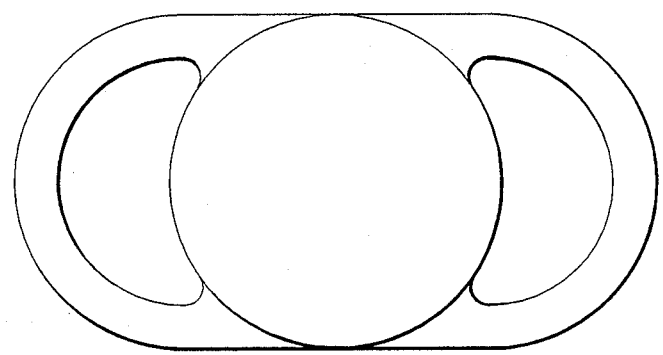
FIG. 9 is a plan view of a bottom part of a mold useful in forming a one piece IOL in accordance with the present invention.

To produce an IOL 10 with the lens body 16 having the foregoing characteristics, and as further depicted in FIGS. 7, 8A and B and 9, the syrup, crosslinking agent and initiator (in the indicated percent by weight concentrations) are mixed, deareated and the resulting mixture poured into a mold such as mold number 1 or 2 illustrated in FIG. 8A and B or the mold illustrated in FIG. 9. With respect to molds of FIG. 8, the resulting mixture is poured onto an aluminum plate 1 bounded by rubber gaskets 2. A glass plate 3 is placed on top of the rubber gaskets and the combination clamped together by clamps 4. The mold is placed in an oven, heated to about 60° C. and cured for about 16 hours. The mold is then post cured at about 90° C. for 24 hours.

After curing, the mold is disassembled and the sheets formed therein made ready for cutting into cylindrical lens blanks in the case of mold number 1 or deflashing into lens bodies in the case of mold number 2. Alternatively, the mold bottom shown in FIG. 9 may be used. As illustrated, the mold has slots machined into its aluminum base to accommodate the haptics at an appropriate angle. The molded part from the mold of FIG. 9 comprises the optic and the haptic elements encased in a thin sheet of flash which may be machined off to produce the finished IOL.

Such cutting and machining to produce the desired IOL may involve conventional milling and lathe techniques with the exception that the part is held at a temperature well below room temperature and preferably between −80° and −10° C. Specifically, it is desired that the material be held below its Beta-relaxation temperature during cutting. Preferably, during cutting, the low temperature environment is formed by exposing the part to a liquid nitrogen spray which maintains the part within the desired temperature range and provides the desired moisture for the cutting operation. As previously noted, at or below its Beta-relaxation temperature, the copolymer material possesses a particularly hard characteristic suitable for high speed and efficient cutting.

An example of a procedure used to fabricate a multipiece IOL as shown in FIG. 1 including separate haptics is as follows. First, flat sheets of the crosslinked acrylic are molded at a thickness of between 2 mm and 8 mm as described above and mounted on holders. The material is then cut into disks which are lathe cut at the low temperatures previously described to form the curved planar surfaces and edge cut. The resulting lens bodies are soaked in Freon and chlorofluoro hydrocarbon solvent for 20 minutes and then dried for 30 minutes in a vacuum oven at 60° C. The curved surfaces of the lens bodies are then polished at a low temperature. Next, the lens bodies are mounted for drilling of the positioning holes 32 as well as the edge holes for receiving the haptics 18. The positioning holes are typically 0.3 mm while the edge holes for receiving the haptics are typically 0.1 mm in diameter. To mount the haptics into the edge holes, the haptics are located in a stainless steel needle and one end of the haptic melted to form a thickened blunt tip. The needle is then inserted into the edge hole to force the blunt end of the haptic into the hole at room temperature. The needle is carefully withdrawn allowing the walls of the edge hole to collapse back to their normal position clamping the haptic in place. This operation is then repeated for the other haptic.

Alternatively, for lens bodies molding using mold number 2 illustrated in FIG. 8B, the sheet is cored in the area of the lens bodies to cut the lens bodies from the sheet. The resulting lens bodies are then mounted in suitable holders and the foregoing procedure repeated.

Finally, for parts molded from the mold illustrated in FIG. 9, the flash may be removed on a mill to form the desired one piece IOL.

From the foregoing, it should be appreciated that the IOLs of the present invention may be provided in various geometries adapted for folding or rolling, etc. to a reduced profile configuration thereby permitting implantation into the eye through an incision of reduced size. Within the eye, the deformed lens returns to its original nondeformed state. However, according to the invention, the lens is formed from a material having a combination of excellent elastic memory and slow speed of retraction characteristics. The lens thus returns slowly to the nondeformed state without injuring eye tissue while achieving the final nondeformed state without creases, wrinkles, or other structural deviations which would otherwise result in optical distortions.

A variety of further modifications and improvements to the invention described herein are believed to be apparent to those skilled in the art. Accordingly, no limitation is intended by way of the description herein, except as set forth in the appended claims.

I claim:

1. A deformable-elastic intraocular lens (IOL), comprising:
   a deformable-elastic lens body of crosslinked acrylic material comprising copolymers of methacrylate and a acrylate esters which are relatively hard and relative soft at body temperature, crosslinked with a diacrylate ester wherein the crosslinked acrylic material has a substantially tack-free surface, a crosslink density of between $0.5 \times 10^{-2}$ and $1.5 \times 10^{-2}$ moles per liter, a glass transition temperature between $-30°$ and $25°$ C., a tensile modulus between 1000 and 3000 psi and an elongation at break of at least 100%; and
   flexible haptics attached to the lens body to position the lens body in the eye.

2. The IOL of claim 1 wherein the lens body is formed by chemically crosslinking the diacrylate ester with a partially polymerized mixture of the copolymers, curing the crosslinked acrylic and holding the cured crosslinked acrylic at a temperature below its Beta-relaxation temperature while machining the lens body.

3. The IOL of claim 2 wherein each haptic is attached by forcing an enlarged end thereof into a smaller hole in an edge of the lens body.

4. A deformable-elastic intraocular lens (IOL), comprising:
   a deformable-elastic lens body of crosslinked acrylic material formed by mixing copolymers of methacrylate and acrylate esters which are relatively hard and relatively soft at body temperature, with a diacrylate ester to produce an acrylic material having crosslinked density of between $0.5 \times 10^{-2}$ and $1.5 \times 10^{-2}$ moles per liter and a glass transition temperature of between $-30°$ and $25°$ C.; and
   flexible haptics attached to the lens body to position the lens body in the eye.

5. The IOL of claim 4 wherein the copolymers are mixed and partially polymerized before mixing with the diacrylate ester.

6. A deformable-elastic intraocular lens body of a crosslinked acrylic material comprising copolymers of methacrylate and acrylate esters which are relatively hard and relatively soft at body temperature, crosslinked with a diacrylate ester wherein the acrylic material has a substantially tack-free surface, a crosslink density of between $0.5 \times 10^{-2}$ and $1.5 \times 10^{-2}$ moles per liter, a glass transition temperature between $-30°$ and $25°$ C., a tensile modulus between 1000 and 3000 psi and an elongation at break of at least 100%.

7. A deformable-elastic intraocular lens body of a crosslinked acrylic material formed by reacting copolymers of methacrylate and acrylate esters which are relatively hard and relatively soft at body temperature to produce a reaction product having a glass transition temperature between $-30°$ and $25°$ C., partially polymerizing the reaction product and mixing it with a diacrylate ester to produce a crosslinked acrylic having a crosslink density of between $0.5 \times 10^{-2}$ and $1.5 \times 10^{-2}$ moles per liter, curing the acrylic and machining the lens body therefrom.

8. The lens body of claim 7 wherein the relatively hard methacrylate ester is a fluoroacrylate.

9. The lens body of claim 7 wherein reaction product comprises ethyl methacrylate, trifluoro ethyl methacrylate and an acrylate ester present in percent by weight concentrations of 25 to 45, 5 to 25 and 30 to 60%, respectively.

10. The lens body of claim 9 wherein the acrylate ester is selected from n-butyl acrylate, ethyl acrylate and 2-ethyl hexyl acrylate.

11. The lens body of claim 10 wherein the diacrylate ester is present in a percent by weight concentration of 0.5 to 3.0%.

12. The lens body of claim 11 wherein the diacrylate ester is selected from ethylene glycol dimethacrylate, propylene glycol dimethacrylate, and ethylene glycol diacrylate.

13. A method of forming a deformable-elastic intraocular lens body comprising the steps of:
   (a) mixing copolymers of methacrylate and acrylate esters which are relatively hard and relatively soft at body temperature;
   (b) partially polymerizing the product of Step (a);
   (c) chemically crosslinking the product of Step (b) with a diacrylate ester;
   (d) curing the product of Step (c); and
   (e) forming a lens body having a predetermined optical characteristic from the product of Step (d).

14. The method of claim 13 wherein Step (e) comprises holding the product of Step (d) at a temperature below its Beta-relaxation temperature while machining the lens body.

15. The method of claim 13 wherein the methacrylate and acrylate esters are mixed together in approximately a 45 to 55% by weight ratio.

16. The method of claim 15 wherein the diacrylate ester of Step (c) is present in a percent composition by weight of 0.5 to 3.0%.

17. The method of claim 16 further including the mixing of a UV-absorber and a free radical initiator in Step (a).

18. The method of claim 13 wherein the relatively hard methacrylate ester is a fluoroacrylate.

19. The method of claim 18 wherein Step (a) further includes mixing the fluoroacrylate in a concentration range by weight of between 5 and 25% with ethyl methacrylate in a concentration range by weight of between 25 and 45% and an acrylate ester selected from n-butyl acrylate, ethylacrylate or 2-ethyl hexyl acrylate in a concentration range by weight of between 30 and 60%.

20. The method of claim 19 wherein the fluoroacrylate is trifluoro ethyl methacrylate.

21. The method of claim 20 wherein Step (a) further includes the mixing of a UV-absorber in a concentration range by weight of between 0 and 10% and a free radical initiator in a concentration range by weight of 0.05 and 0.2%.

* * * * *